United States Patent [19]

Yamaguchi et al.

[11] Patent Number: 4,612,936

[45] Date of Patent: Sep. 23, 1986

[54] CLIP-TYPE ELECTRODE FOR ELECTROCARDIOGRAPHS

[75] Inventors: Kimio Yamaguchi, Tokyo; Yoshinori Chiba, Kashiwa, both of Japan

[73] Assignee: Fukuda Denshi Co., Ltd., Tokyo, Japan

[21] Appl. No.: 644,902

[22] Filed: Aug. 28, 1984

[30] Foreign Application Priority Data

Apr. 12, 1984 [JP] Japan .................. 59-54009[U]

[51] Int. Cl.⁴ .............................................. A61B 5/04
[52] U.S. Cl. ..................................... 128/644; 128/802
[58] Field of Search ............... 128/639, 644, 802, 346, 128/640–643

[56] References Cited

U.S. PATENT DOCUMENTS

| | | | |
|---|---|---|---|
| 1,640,061 | 8/1927 | Wappler | 128/802 |
| 1,644,803 | 10/1927 | Wappler | 128/802 |
| 2,611,368 | 9/1952 | Pecora | 128/639 |
| 2,782,786 | 2/1957 | Krasno | 128/639 |
| 2,831,174 | 4/1958 | Hilmo | 128/639 X |
| 3,067,749 | 12/1962 | Walters | 128/639 |
| 3,323,516 | 6/1967 | Salter | 128/644 |
| 3,981,308 | 9/1976 | Schlein | 128/346 |
| 4,466,437 | 8/1984 | Dyck et al. | 128/346 X |

FOREIGN PATENT DOCUMENTS

| | | | |
|---|---|---|---|
| 0204616 | 12/1983 | Fed. Rep. of Germany | 128/644 |
| 2133884 | 8/1984 | United Kingdom | 128/644 |

Primary Examiner—Kyle L. Howell
Assistant Examiner—Angela D. Sykes
Attorney, Agent, or Firm—Armstrong, Nikaido, Marmelstein & Kubovcik

[57] ABSTRACT

A clip-type electrode includes a pair of clamping plates arranged to be opened and closed relative to each other about a common shaft and having concave surfaces facing each other, an electrode member mounted on one of the clamping plates, and a spring coiled around the common shaft for biasing the ends of the clamping plates remote from the common shaft towards each other. One of the clamping plates is longer than the other. The electrode member includes a strip of resilient, electrically conductive material bent into a U-shaped cross-section thus providing a pressuring plate section for applying pressure to the limb of a patient, and a pair of engagement plates each extending upwardly from opposing edges of the pressuring plate section and having plural inwardly projecting bosses. The engagement plates clamp the longitudinal edges of the longer one of the clamping plates for attaching the electrode member to the clamping plate. The pressuring plate section is brought into intimate contact with the surface of the skin of the patient's limb to make the contact resistance uniform and eliminate noise or distortion in the output waveform, thereby making possible accurate diagnosis of the condition of the heart. Since one of the pair of the clamping plates is longer than the other, the electrode is unlikely to be detached by movement of the limb.

4 Claims, 5 Drawing Figures

CLIP-TYPE ELECTRODE FOR ELECTROCARDIOGRAPHS

BACKGROUND OF THE INVENTION

This invention relates to an electrode used in an electronic instrument, such as an electrocardiograph, adapted to measure the state of a living body, and more particularly to a clip-type electrode used in an electrocardiograph.

An electrocardiograph is widely utilized to diagnose the heart of a human or other living body. In operation, a minute electric current induced in the surface of the skin of, e.g., the human body, is applied to an electrocardiograph composed of electronic circuitry external to the body. The electrocardiograph measures and observes changes in electrical potential caused by changes in the minute current ascribable to the heartbeat. Based on the results of such analysis, the doctor can make a diagnosis on whether or not the patient's heart is functioning normally.

FIG. 1 shows a system for measuring changes in electrical potential by using an electrocardiograph. In the drawing, numeral 1 designates an electrocardiograph composed of electronic circuitry. A lead 2 is connected from the electrocardiograph 1 to an electrical distributor 3 from which four leads $4_1$, $4_2$, $4_3$, and $4_4$ are connected to one end of respective clip-type electrodes $5_1$, $5_2$, $5_3$ and $5_4$ clipped to the wrists and ankles of a patient lying lengthwise on a bed, not shown. The other ends of the clip-type electrodes $5_1$, $5_2$, $5_3$ and $5_4$ are respectively connected to leads $6_1$, $6_2$, $6_3$ and $6_4$ and thence to a display unit 7 such as a CRT.

In the above-described system, changes in the electrical potential induced in the wrists and ankles of the human body are sensed by the clip-type electrodes $5_1$, $5_2$, $5_3$ and $5_4$ and displayed by the display unit 7. Based on the voltage waveform on the display unit, the doctor may make a diagnosis on whether the heart function is normal or abnormal.

In the foregoing system, the wrists and ankles to which the clip-type electrodes $5_1$, $5_2$, $5_3$ and $5_4$ are attached are not truly cylindrical in shape and differ in thickness from one patient to another. The thickness also differs with one and the same patient depending on the positions at which the electrodes $5_1$ to $5_4$ are attached.

FIG. 2 shows the construction of a prior-art clip-type electrode. As shown, the electrode 5' comprises a pair of curved clamping plates 8, 8' adapted to be clipped on a wrist or ankle. These plates 8, 8' are biased by a spring 5b disposed on a shaft 5a so that the ends of the plates are caused to approach each other. An electrode plate 9 is affixed to the inner surface of the clamping plate 8 by a fastener such as nut. A pair of terminals 10, 10' provided on the outside of the clamping plate 8 are connected to the electrode plate 9.

The above described clip-type electrode 5' is manually grasped at the rear part of the clamping plates 8, 8' so that the forward parts of the clamping plates 8, 8' are opened by pivoting about the shaft 5a for attachment to the wrist or ankle of the human body.

When the foregoing clip-type electrode 5' is attached to the wrist or ankle for taking an electrocardiogram, the electrical potential is measured at various positions of the wrist or ankle. However, with movement of a wrist or ankle, the clip-type electrode fastened thereto also is shifted in such a manner that the clamping plates 8, 8' are moved on the surface of the wrist or ankle. The result is that the electrode plate 9 may be detached from the surface of the skin or contact the skin surface only poorly. If the electrode plate 9 becomes detached from the skin or fails to make good contact with the skin, there is an increase in the contact resistance between the surface of the skin and the electrode plate 9, thereby resulting in a distorted cardiogram waveform or noise.

Also, when the wrist or ankle is shifted while the clip-type electrode 5' remains attached thereto, the electrode 5' may become disengaged from the wrist or ankle thus making it impossible to measure the difference in electrical potential.

SUMMARY OF THE INVENTION

An object of the present invention is to provide a clip-type electrode free of the abovementioned disadvantages encountered in the prior art.

Briefly, the present invention provides a clip-type electrode for an electrocardiograph comprising a pair of clamping plates adapted to be opened and closed about a common shaft and having concave surfaces facing each other, an electrode member mounted on one of the clamping plates, and a spring coiled around the common shaft for biasing the ends of the clamping plates remote from the common shaft towards each other. One of the clamping plates is longer than the other. The electrode member includes a strip of resilient, electrically conductive material which is bent into a U-shaped cross-section thus providing a pressure plate section for pressing the limb of the patient, and a pair of engagement plates each upstanding from opposing edges of the pressure plate section and having plural inwardly projecting bosses. The engagement plates clamp the opposing longitudinal edges of the longer one of the clamping plates to attach the electrode member to the clamping plate.

In the above construction of the clip-type electrode for electrocardiographs, the pressure plate section of the electrode member remains in intimate contact with the surface of the skin even when the limb such as the wrist or ankle clamped by the pair of clamping plates is moved, and the clamping plates do not detach themselves from the limb. This allows a correct diagnosis of heart function to be given.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

Figure 1:
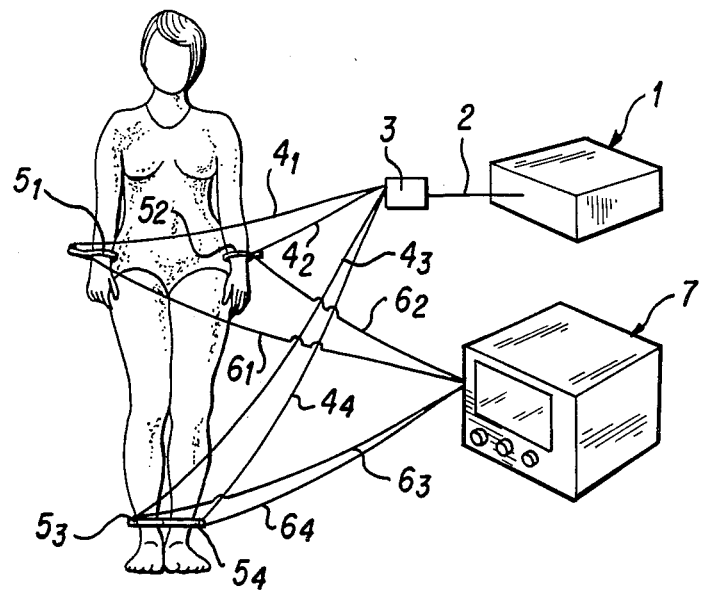
FIG. 1 is a schematic view showing a system for measuring changes in the electrical potential of a human body with the aid of an electrocardiograph.
Figure 2:
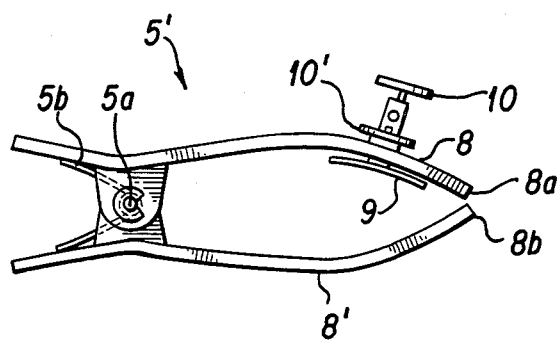
FIG. 2 is a side view showing the construction of the prior-art clip-type electrode.
Figure 3:
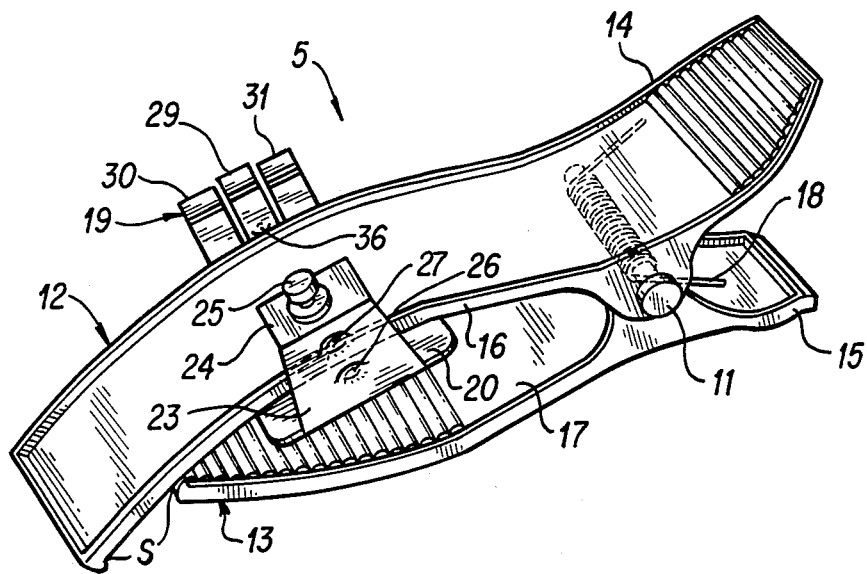
FIG. 3 is a perspective view showing the construction of the clip-type electrode according to the present invention.
Figure 4:
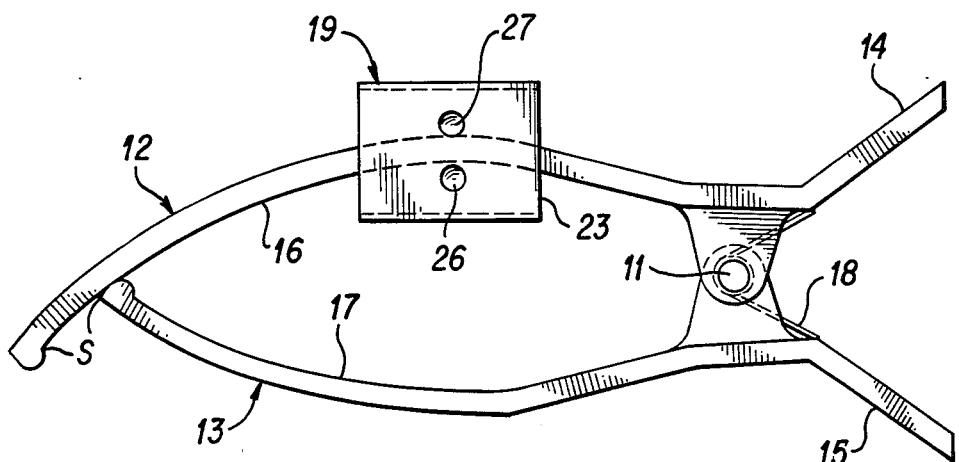
FIG. 4 is a side view showing the electrode illustrated in FIG. 3.
Figure 5:
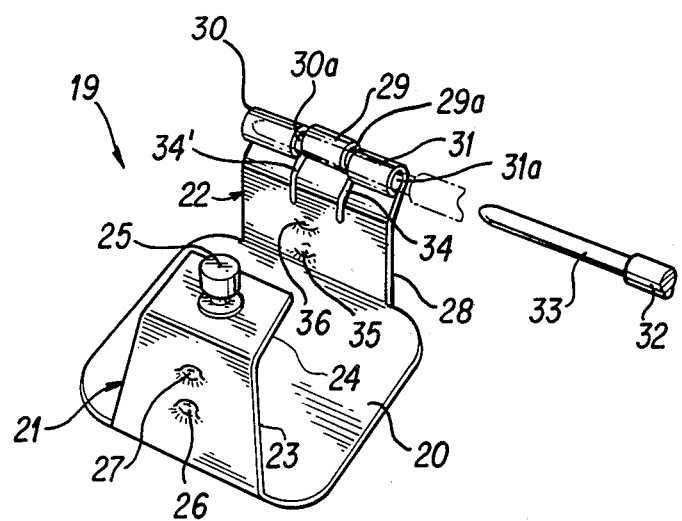
FIG. 5 is a perspective view showing the construction of an electrode member.

FIG. 3 shows an embodiment of a clip-type electrode according to the present invention. FIG. 4 shows the same clip-type electrode in side elevation, while FIG. 5 shows the construction of the electrode member or electrode proper in a perspective view. The clip-type electrode is constructed of a pair of curved clamping plates 12, 13 that may be turned relative to each other about a shaft 11. Rearwardly of the shaft 11, the plates 12, 13 are formed as outwardly bent grasping sections 14, 15 having knurled surfaces to facilitate hundling of the electrode. Forwardly of the shaft 11, the clamping plates 12, 13 are formed as curved clamping sections 16, 17 presenting concave surfaces facing each other. These clamping sections 16, 17 clamp the limb of a living body, such as a wrist or ankle of a human patient. A coil spring 18 is disposed around the shaft 11 and has its free end parts abutting against the inner surface of the grasping sections 14, 15 for biasing the clamping plates 12, 13 to close the foremost parts of the clamping plates 12, 13 toward each other. The length of the clamping section 16 of the one clamping plate 12 is longer by a value S than the length of the clamping section 17 of the other clamping plate 13. The inner surfaces of the clamping sections 16, 17 are also knurled to prevent slipping when the limb such as the wrist or ankle is clamped by these sections.

An electrode member 19 is mounted on the clamping plate 12 so as to clamp both edges of the clamping plate 12. The electrode member 19 is formed of resilient, electrically conductive metallic material and, as illustrated in FIG. 5, comprises a substantially rectangular flat pressure plate section 20 adapted to be pressed against the limb of the living body, and a pair of engagement plate sections 21, 22 directed upwardly from both edges of the plate section 20. The engagement plate section 21 comprises an upright plate 23 and a top plate 24 contiguous thereto and bent inwards parallel to the flat pressure plate section 20. A screw-type terminal 25 is provided approximately centrally of the top plate 24 and connected to one end of an electrical lead the other end of which is connected to the display unit 7.

The inner surface of the upright plate 23 is formed to include a first boss 26 projecting towards the opposite engagement plate section 22 at a predetermined distance from the flat plate section 20, and a second boss 27 projecting in a similar manner at a predetermined distance from the first boss 26.

The engagement plate section 22 comprises an upright plate 28 and trifurcated support parts or tongues 29, 30 and 31 divided from one another by slits 34, 34'. The intermediate tongue 29 is biased slightly outwards with respect to the two terminal tongues 30, 31. When an electrode rod 33 is introduced into tubular insertion openings 29a, 30a and 31a of the tongues 29, 30 and 31, the rod 33 is pressed by the tongue 29 biased in the above described manner so that it can be positively held in the openings 29a, 30a and 31a without the risk of accidental removal.

The inner surface of the upright plate 28 of the engagement plate section 22 is formed to include a first boss 35 projecting towards the engagement plate section 21 at a predetermined distance from the flat plate section 20, and a second boss 36 projecting in a similar manner at a predetermined distance from the first boss 35. The first boss 26 provided on the upright plate 23 is in register with the first boss 35 provided on the upright plate 28, while the second boss 27 provided to the upright plate 23 is in register with the second boss 36 provided on the upright plate 28. The electrode member 19 is fixedly mounted on the clamping plate 12 with the first bosses 26, 35 and the second bosses 27, 36 holding the longitudinal edges of the clamping plate 12.

The method of using the above-described clip-type electrode 5 will now be described. With the engagement plate sections 21, 22 of the electrode member 19 shown in FIG. 5 spread apart from each other, the electrode member 19 is mounted on the clamping plate 12 in such a manner that the first bosses 26, 35 and second bosses 27, 36 clamp the side edges of the clamping plate 12 and the flat plate section 20 is positioned between the clamping sections 16 and 17. At this time, the electrode member 19 is supported by the first bosses 26, 35 and the second bosses 27, 36 and is tiltable with respect to the clamping plate 12. The grasping sections 14, 15 are gripped manually for spreading the foremost parts of the clamping plates 12, 13 apart from each other. After the limb such as the wrist or ankle is introduced between the clamping sections 16, 17, the manual pressure on the holding sections 14, 15 is released, so that the limb is clamped by the clamping sections. Since the electrode member 19 is tiltable at this time, the pressure plate section 20 can be intimately contacted with the skin surface of the limb.

With the clip-type electrode 5 thus fastened to the limb, the difference in electrical potential is measured while the position of the limb is changed. Since the clamping section 16 is longer by S than the clamping section 17, the clamping plate 12 is capable of moving in accordance with limb movement and the flat plate section 20 of the electrode member 19 can be brought into intimate contact with the skin surface of the limb for stable electrical contact therewith. The result is that the contact resistance between the pressure plate section 20 of the electrode part 19 and the surface of the skin does not change but remains stable so that the output voltage waveform is not distorted or affected by noise.

From the foregoing it is seen that the arrangement of the present invention provides a clip-type electrode for use with an electrocardiograph, according to which one of the pair of holding sections is longer than the other section so as to permit the clamping plates to move with the movement of the limb while also permitting the electrode member to be tilted with respect to the clamping plate to which it is attached in such a manner that the pressure plate section can be brought into intimate contact with the surface of the skin while the contact resistance is stable. This allows heart function to be diagnosed more accurately without the adverse influence of noise or a distorted waveform ascribable to a variation in contact resistance.

Since one of the clamping plates has its clamping section longer than the other section, the limb is less likely to free itself of the clip-type electrode in comparison with the conventional clip-type electrode having clamping sections of equal lengths.

In addition, the electrode member can be attached to the clamping plate very easily merely by spreading the engagement plate sections provided on both sides of the flat pressure plate section slightly outwardly to hold the longitudinal edges of the clamping plate.

As many apparently widely different embodiments of the present invention can be made without departing from the spirit and scope thereof, it is to be understood that the invention is not limited to the specific embodiments thereof except as defined in the appended claims.

What we claim is:

1. A clip-type electrode for an electrocardiograph comprising:

a pair of clamping plates arranged to be opened and closed relative to each other about a common shaft extending laterally therebetween, said clamping plates having concave surfaces facing each other, an electrode member mounted on one of said clamping plates, and a spring means coiled around said common shaft and arranged to bias ends of said clamping plates remote from said common shaft towards each other, one of said clamping plates being longer than the other, said electrode member being formed of an electrically conductive resilient material and including a pressure plate section for pressing a limb of a living body, and a pair of engagement plates each extending upwardly from opposing edges of said pressure plate section and having plural inwardly projecting bosses, said engagement plates clamping opposing longitudinal edges of the longer one of said clamping plates for attaching said electrode member to said last-mentioned clamping plate.

2. A clip-type electrode according to claim (1), wherein a distal end of one of said engagement plates is bent to form a top plate section provided with a central terminal, while a distal end of the other of said engagement plates is divided by slits into plural supporting tongues having substantially aligned insertion openings for resilient insertion of an electrode rod.

3. A clip-type electrode as claimed in claim 2, wherein an intermediate one of said plural supporting tongues is formed so that its insertion opening is slightly displaced from alignment with said insertion openings of other supporting tongues, whereby an electrode inserted therein is pressed to be positively held therein.

4. A clip-type electrode as claimed in claim 2, wherein said electrode member is formed so that it may be engaged to said clamping plate longitudinal edges at any position longitudinally along said clamping plate.

* * * * *